(12) United States Patent
Schmiedel et al.

(10) Patent No.: US 6,623,943 B2
(45) Date of Patent: Sep. 23, 2003

(54) PROCESS FOR PREPARING RESISTANT STARCH

(75) Inventors: Detlef Schmiedel, Berlin (DE); Bärbel Johanna König, Busendorf (DE); Gisela Jacobasch, Wandlitz (DE)

(73) Assignee: Bayer Corporation GmbH, Frankfurt (DE)

( * ) Notice: Subject to any disclaimer, the term of this patent is extended or adjusted under 35 U.S.C. 154(b) by 0 days.

(21) Appl. No.: 09/522,212

(22) Filed: Mar. 9, 2000

(65) Prior Publication Data

US 2003/0054501 A1 Mar. 20, 2003

(30) Foreign Application Priority Data

Mar. 12, 1999 (DE) .......................... 199 11 001

(51) Int. Cl.⁷ .......................... C12P 19/16; C08B 30/00
(52) U.S. Cl. .......................... 435/98; 435/101; 536/102; 536/124; 426/549; 426/661; 426/28; 127/38; 127/71
(58) Field of Search .................... 435/101, 98; 536/102, 536/124; 426/549, 661, 28; 127/38, 71

(56) References Cited

U.S. PATENT DOCUMENTS 6,013,299 A * 1/2000 Haynes et al. .............. 426/549

FOREIGN PATENT DOCUMENTS

| EP | 0529894 | 3/1993 |
|----|---------|--------|
| EP | 0564893 | 10/1993 |
| EP | 0688872 | 12/1995 |
| EP | 0846704 | 6/1998 |
| WO | WO 90/15147 | 12/1990 |
| WO | WO 96/34968 | 11/1996 |
| WO | WO 97/47657 | 12/1997 |
| WO | WO 99/22606 | 5/1999 |
| WO | WO 00/02926 | 1/2000 |

OTHER PUBLICATIONS

*Starch: Chemistry & Technology*, Whistler et al, editors, Academic Press, Inc., New York, pp. 49–56, 1984.*

Schmidel et al.; Starch/Stärke, 49 (1997); No. 9, pp. 371–379.

Enzyme–Resistant Starch. II. Differential Scanning Calorimetry Studies On Heat–Treated Starches and Enzyme Resistant Starch Residues, vol. 67, No. 3, May 1, 1990, pp. 217–221, also referred to as XP000647641.

* cited by examiner

*Primary Examiner*—Francisco Prats
(74) *Attorney, Agent, or Firm*—Frommer Lawrence & Haug LLP

(57) ABSTRACT

The present invention relates to a process for preparing resistant starch, the resistant starch obtainable from this process and use thereof.

11 Claims, No Drawings

PROCESS FOR PREPARING RESISTANT STARCH

The present invention relates to a process for preparing resistant starch of type 3, the resistant starch obtainable from this process and its use.

The use of resistant starch (RS,) is gaining increasing importance in the food industry. The organism obtains energy only to a small extent from the breakdown of RS-containing products. This energy supply relates exclusively to the oxidative degradation of adsorbed short-chain fatty acids from the large intestine. These short-chain fatty acids are end products of the carbohydrate metabolism of the intestinal microflora. The intake of RS-containing foods provides substrates for the energy metabolism of the intestinal microflora and the large-intestine epithelial cells. The latter, to maintain their structure and function, depend on the luminal supply of short-chain fatty acids and, in particular, butyrate.

U.S. Pat. No. 3,729,380 discloses that the proportion of highly branched amylopectin can be reduced by enzymatic treatment with debranching enzymes and starch debranched in this manner has a stronger tendency to retrogradation than native starch.

In retrogradation (also termed crystallization), what are termed α-amylase-resistant starch structures form, which are termed "resistant starch" (RS), i.e. they are not degraded by α-amylases. A distinction is made between the following types of resistant starch:

$RS_1$ starch physically inaccessible to digestion, e.g. in undigested plant cells or starch granules $RS_2$ indigestible starch granules, e.g. raw potatoes, green bananas etc.

$RS_3$ indigestible retrograded starch, e.g. as a result of thermal and/or enzymatic treatment, such as bread, cooked potatoes etc.

$RS_4$ indigestible chemically modified starch, e.g. due to crosslinking or esterification (acetylation etc.) etc.

RS, in foods or food compositions, because of their decreased ability to be metabolized are a reduced-energy component supplying body in the sense of a dietary fiber or what is termed a "fat replacer".

In contrast to $RS_4$, the RS types 1 to 3 can be made accessible to alpha-amylase degradation by dissolution in NaOH or dimethyl sulfoxide.

EP-A-0 564 893 describes a process for preparing an Re-containing product by gelatinizing a roughly 15% strength aqueous suspension of a starch which consists of at least 40% amylose, treating it with a debranching enzyme and then retrograding the resultant intermediate product. The product comprises at least 15% RS. If, in this process, a starch having an amylose content of 100% is used, the product comprises about 50% RS.

EP-A-0 688 872 describes a process for preparing a product comprising 25 to 50% RS from an approximately 20% strength aqueous suspension of a so-called "partially degraded", gelatinized starch$_1$, and a maltodextrin, which are enzymatically debranched and then retrograded. In the process, the starting material used is a starch having an amylose content of less than 40%.

"Partially degraded" starch in EP-A-0 688 872 means a starch which has been reduced in molecular weight by suitable physical or chemical treatment, the shortening in chain length effecting both the amylose and also the amylopectin. The degradation includes both hydrolysis processes (acid- or enzyme-catalyzed) and extrusion, oxidation or pyrolysis.

The debranching enzymes used in EP-A0 688 872 are pullulanases and isoamylases. After the enzymatic treatment, the retrogradation is performed in a temperature range from 0 to 30° C. and a time period of 1 to 3 days, by allowing the aqueous reaction product to stand. The process product is then dried by spray-drying. The pulverulent product has an RS content of up to 60% (w/w).

EP-A-0846704 describes a retrograded starch which consists of more than 55% readily-fermentable resistant starch, more than 50% of which is composed of chains having a DP between 10 and 35 and has a DSC melting temperature of below 115° C., EP-A-0846704 sets forth that the extent of retrogradation of the starch increases with the amylose content in the starch, whereas a high amylopectin content in the starch counteracts the formation of RS.

The object of the present invention is to provide an alternative preparation process for resistant starch (RS) or compositions comprising RS which offers the advantages of an economic process procedure or makes it possible to prepare RS-containing products in improved quality and quantity.

The process of the invention uses as starting material for this, in addition to conventionally available starches from potatoes, corn, wheat, peas, soy and/or sweet potatoes, preferably potatoes, corn and/or wheat, in particular also vegetable starches which have been modified by genetic engineering methods, preferably with respect to their side-chain distribution and in particular those from potatoes, corn and/or wheat, especially so-called waxy starches. Genetically modified starches of this type are disclosed, for example, by the patent applications or patents below: WO 90/12876-A1, WO 91/19806-A1, WO 92/11375-A1, WO 92/11376-A1, WO 92/11382-A1, WO 92/14827-A1, WO 94/09144-A1, WO 94/11520-A1, WO 95/04826-A1, WO 95/07355-A1, WO 95/26407-A1, WO 95/34660-A1, WO 95/35026-A1, WO 96/15248-A1, WO 96/19581-A1, WO 96/27674-A1, WO 96/34968-A1, WO 97/04112-A1, WO 97/04113-A1, WO 97/11188-A1, WO 97/16554-A1, WO 97/20040-A1, WO 97/22703-A1, WO 97/45545-A1, WO 98/11181-A1, WO 98/15621-A1, WO 98/37213-A1, WO 98/37214-A1 and also CA 2,061,443, DE 19820607.0, DE 19820608.9, DE 19836097.5, DE 19836098.3, DE 19836099.1, EP-A-0 521 621, EP-A-0 703 314, EP-A-0 737 777, EP-A-0 779 363 or U.S. Pat. No. 5,300,145. In a particular embodiment of the process of the invention, what are termed waxy starches are used to prepare RS.

The present invention, surprisingly, makes it possible to prepare resistant starch of type 3 (RS) or RS products (i e. compositions comprising RS) in relatively high quantity and/or quality which can advantageously be used in a varied manner to prepare foods, food compositions and food precursors and which also resist thermal stress. Particularly surprisingly, the present invention makes it possible to prepare RS or RS products having high thermally stability from what are termed waxy starches, The present invention thus relates to a process for preparing resistant starch, in which a) a suspension is prepared from starch and water in a concentration range of about 5–50%;

b) said suspension is gelatinized by heating and then cooled;

c) the pH of the resultant suspension from b) is set to about 3–7.5 and the solids content to about 5–50%;

d) the suspension is again heated to a maximum of 150° C. and finally e) is cooled stepwise or gradually at a rate of 0.1–10 K/min, preferably 0.5–5 K/min, preferably under the action of shear forces.

If appropriate the starch used in the process of the invention can be debranched enzymatically using debranching enzymes (e.g. isoamylases, pullulanases or other debranching enzymes) and then the debranching enzyme or enzymes can be inactivated or removed, preferably after setting the pH as specified in step c) of the process according to the invention.

In a particularly preferred embodiment of the process according to the invention, the intermediate obtained after step b) is freed from buffer salts, in particular from acetate, i.e. is washed salt-free or acetate-free.

In a further embodiment of the process according to the invention, a further process step follows, in which the process product is subjected, under conditions of water excess, to a hydrothermal treatment (annealing) below the conversion temperature, preferably below about 65–70° C.

If desired, the intermediate obtained after step b) and/or the resultant RS product can be dried, e.g. by spray-drying, freeze drying or other drying processes known to those skilled in the art In the context of the present invention the RS content is the content of alpha-amylase-resistant starch polysaccharides, as can be determined by the method of Englyst et al. (Classification and measurement of nutritionally important starch fractions, Europ. J. Clin. Nutr. (1992) 46 (Suppl. 2), p. 33-p. 50). Preferably, in the process of the invention, starch is used as starting material, preferably starch from corn, wheat and/or potatoes, in particular a waxy starch.

Other preferred starting starches are starches from genetically modified plants, preferably from corn, wheat and potatoes and very particularly those starches which are chemically or physically modified and particularly have been modified with respect to their side-chain distribution. Preferably, the starches to be used according to the invention have, in their side-chain portion, a degree of polymerization (DP) of about 6–100 DP, preferably about 6–60 DP in the A chains, B chains and/or C chains, especially waxy starches.

Other particular preferred modified starches suitable according to the various embodiments of instant invention are modified in that the portion of side chains having a degree of polymerization (DP) of about 50–100 is significantly reduced, i.e. at least 10%, preferably at least 25%, compared to the corresponding unmodified starch.

In a particularly preferred embodiment of the process according to the invention, waxy starches are used as starting material. The term "waxy starch", in the context of the embodiments of the present invention, preferably means starches having an amylose content of about<10%, preferably about<5% and in particular about <3%, very especially preferred starches in this case are those from potatoes, corn and/or wheat, very particularly from potatoes.

In a further particularly preferred embodiment of the process according to the invention, the cooling according to process step e) is performed stepwise (i.e. by holding the temperature constant at intervals) or gradually, preferably in the presence of shear forces (e.g. with stirring or flow) in order to avoid high temperature gradients in the suspension.

The cooling rate which is to be maintained in process step e) during the cooling phases is 0.1–10 K/min, preferably 0.5–5 K/min.

Optionally, a further temperature-holding phase can follow step e) in the process of the invention.

In a further preferred embodiment of the process according to the invention, process step e) is performed stepwise by first cooling at a cooling rate of 0.1–10 K/min, preferably 0.5–5 K/min, to a temperature in the range of about 70–30° C., then maintaining this temperature for a period of about from 10 min to 10 h, cooling again at a cooling rate of 0.1–10 K/min, preferably 0.5–5 K/min, to a temperature in the range of about 30–4° C. and finally maintaining the temperature for a period of 1–100 h, preferably under the action of shear forces.

A further advantage of the process according to the invention is, inter alia, the fact that, from the starting starches described, an aqueous hot paste can be produced which has a solids content up to 30% by weight or more, without a partial degradation, for example acid- or enzyme-catalyzed hydrolysis, extrusion, oxidation or pyrolysis, having to be provided upstream of the process. This leads to a considerable simplification of the process procedure and reduction of the time and cost requirements of the process according to the invention.

In the process of the invention, debranching enzymes such as pullulanase and isoamylase or mixtures thereof can be used for the debranching process. Depending on the nature of the specific enzyme, the debranching process is carried out in a temperature range from 25 to 75° C., preferably from 35 to 65° C., in particular from 40 to 60° C., and at a pH in the range from 3 to 7.5, preferably from 3.5 to 6, As a result of the higher contents obtainable by the novel process of retrogradable polymers and lower contents of low-molecular-weight, non-retrograding oligosaccharides, such as glucose, maltose, maltotriose, maltotetraose, maltapentaose, maltohexaose, maltoheptaose, maltooctaose and/or isoforms of these oligosaccharides, the retrogradation is promoted and leads to an increase in the RS content. The content of rapidly digestible oligosaccharides is markedly reduced compared with conventional maltodextrin preparations, so that a comparatively low-calorie RS product results.

In an embodiment of the process according to the invention, a hot paste (suspension) is produced having a content of the above-described starting materials of about 5–50%, preferably about 5–30%, in particular about 10–20% by weight In addition, a feature of the process according to the invention can be that the hot paste (suspension) is cooled to a temperature in the range around 35 to 75° C. and then or simultaneously with addition of a suitable buffer solution a pH of between 3 and 7.5 is set and a defined amount of an enzyme and/or enzyme mixture (e.g. pullulanase and/or isoamylase) is added that is able to hydrolyze α-1,6-glycosidic bonds of the starch, and this enzyme or enzyme mixture is allowed to act on the starch paste, with or without stirring, for up to 72 h.

In addition, a feature of the process according to the invention can be that, if appropriate after washing the debranched product, a suspension is prepared, this is warmed and/or heated up to 120° C. and then retrograded at a temperature in the range from 60° C. to 0° C., preferably from 35 to 15° C., in particular from 27 to 22° C., from 16 to 0° C. or from 6 to 2° C. and/or for a time period of from 1 to 72 h, preferably from 1 to 36 h, and in particular from 16 to 30 h.

In addition, a feature of the process according to the invention can also be that cooling and retrogradation are performed according to a temperature-step program in a temperature range from 100 to 0° C., and preferably from 90 to 4° C., for a total time period of from 8 to 36 h, preferably from 20 to 28 h, and in particular from 22 to 26 h, according to the following temperature-time program (Table 1), in a stepwise or gradual, linear or nonlinear manner (Tables 2 and 3) with or without the action of shear forces (for example stirring or flow), the time periods selected aggregating to form an above-specified total time period:

TABLE 1

Cooling program 1 (step program with 6 holding temperatures)

| Temperature (° C.) | Holding time |
|---|---|
| 90 | 5 min |
| 80 | 10 min |
| 70 | 10 min |
| 60 | 30 min |
| 40 | 1 h |
| 25 | 22 h |

TABLE 2

Cooling program 2 (gradual cooling at a cooling rate of 1.5 K/min)

| Temperature (° C.) | Temperature profile |
|---|---|
| 100 | constant for 20 min |
|  | 1.5 K/min |
| 50 | constant for 5 h |
|  | 1.5 K/min |
| 25 | constant for 17.83 h |

TABLE 3

Cooling program 3 (gradual cooling at a cooling rate of 3 K/min)

| 100 | constant for 20 min |
|---|---|
|  | 3 K/min |
| 50 | constant for 5 h |
|  | 3 K/min |
| 25 | constant for 18.58 h |

A further subject matter of the invention is also a resistant starch, a composition comprising a resistant starch and/or the resistant starch product which is obtainable by a process according to the invention, preferably from a waxy starch and has a high thermal stability, which features a $T_p$ value of about 95–160° C., preferably about 110–160° C., in particular about 125–160° C., very particular about 145–160° C., or which features a $T_O$-value of about 80–150° C., preferably about 100–150° C., in particular 120–150° C., and which, if appropriate, passes through 2 or more thermal conversions.

An RS which passes through 2 or more thermal conversions for the purposes of the present invention is an RS which has 2 or more peak temperatures $T_p$ in the DSC measurement, The resistant starch product of the invention has an RS content of at least 25%, preferably at least 50%, for preference at least 75% and in particular about 90%.

All percentages of the present application are percentages by weight (% w/w), unless specified otherwise.

A further subject matter of the invention is also the use of vegetable starch, in particular starch from corn, wheat and potatoes, especially starches from genetically modified plants, preferably from corn, wheat and potatoes and very particularly those starches which are chemically or physically modified and have been modified in particular with respect to their side-chain distribution in a process of the invention for preparing resistant starch, Preferably, the starches to be used according to the invention have, in their side-chain portion, a degree of polymerization (DP) of about 6–100 DP, preferably about 6–60 DP in the A chains, B chains and/or C chains, in particular a wax-starch.

Yet a further subject matter of the invention is also the use of resistant starch or a resistant starch product which is obtainable by a process of the invention for preparing resistant starch, a) for producing foods, food compositions or food precursors, b) as fat replacer, And finally, a subject matter of the invention is also a food precursor, a food, a food composition or a fat replacer comprising a resistant starch of the invention or a resistant starch product of the invention, The potato starch types listed in the examples hereinafter have the following meanings:

| | |
|---|---|
| conventional = | starch from potatoes of the cultiver Désireé (wild type) |
| waxy (low P) = | starch from genetically modified potatoes obtainable in accordance with Example 11 of WO 97/11188 A1 |
| waxy (P-Ø) = | starch from genetically modified potatoes transformed using the plasmid pB33-anti-GBSSI described in Example 11 of WO 97/11188 A1 |
| amylose-rich = | starch from genetically modified potatoes obtainable in accordance with Example 10 of WO 97/11188 A1 |

EXAMPLE 1

Determination of the RS Content.

200 mg (dry weight) of a pulverulent product to be analyzed for its RS content were incubated according to the method of Englyst et al. for determination of the RS content for 120 minutes with the described enzyme mixture at pH 5.2. After completion of the enzymatic degradation, the activity of the enzymes was stopped by reducing the pH to 3 and the temperature to 20° C. Then, by adding 4 times the volume of ethanol, an 80% (v/v) ethanolic solution was established. The 80% ethanolic solution was allowed to stand for 1 h at room temperature. The precipitate was centrifuged (2500×g, 10 min) and the supernatant was discarded. The residue was extracted three times with 80% (v/v) ethanol and once with absolute ethanol and then centrifuged. The residue was lyophilized and weighed. The dry matter of the residue was determined and the RS content calculated according to the following equation:

$RS\ [\ ]=100 \times$ weight of the residue (dry weight)/initial weight (dry weight)

EXAMPLE 2–9

Effect of the Retrogradation Temperature and of the Starting Material on the RS Content in the Product.

Hot pastes were produced from debranched products of conventional and genetically modified potato starches. These pastes were set to a solids content of 10% by weight and retrograded for 24 h in a water bath at 4 or 25° C. The retrograded samples were dried and the RS content was determined as described in Example 1. Table 4 illustrates the effect of the retrogradation temperature and the starting material on the RS content in the product produced from 10% strength pastes (suspensions) of the debranched products used by retrogradation for 24 hours.

TABLE 4

Effect of temperature and of the starting material on the RS content

| Example | Potato starch type (debranched) | Retrogradation temperature (° C.) | RS [% by weight] |
|---|---|---|---|
| 2 | conventional | 4 | 50 |
| 3 | conventional | 25 | 52 |
| 4 | waxy (low P) | 4 | 59 |

TABLE 4-continued

Effect of temperature and of the starting material on the RS content

| Example | Potato starch type (debranched) | Retrogradation temperature (° C.) | RS [% by weight] |
|---|---|---|---|
| 5 | waxy (low P) | 25 | 59 |
| 6 | waxy (P-Ø) | 4 | 78 |
| 7 | waxy (P-Ø) | 25 | 79 |
| 8 | amylose-rich | 4 | 47 |
| 9 | amylose-rich | 25 | 56 |

Examples 2 to 9 in Table 4 make it clear that the retrogradation temperature has only a small effect on the RS content in the products. Rather, the starting material is critical for the level of the RS content in the product, Debranched products of conventional and amylose-rich potato starches have a lesser tendency toward RS formation due to retrogradation of 10% strength pastes than corresponding debranched products from potato starch of a waxy variety. Among the waxy varieties, that having an average phosphate content (P-Ø) is more suitable for preparing RS, compared with that of low-phosphate (low-P), if the solids content in the retrograded paste is 10%,

EXAMPLES 10–17

Effect of the Solids Content and of the Starting Material on the RS Content

Table 5 illustrates the effect of the solids content and of the starting material on the RS content in the product produced from 10 and 30% strength pastes of the above-mentioned debranched products by retrogradation for 24 hours,

TABLE 5

Effect of the solids content in the paste and of the starting material on the RS content

| Example | Potato starch type (debranched) | Temperature [° C.] | Solids content 10% by weight RS [% by weight] | 30% by weight RS [% by weight] |
|---|---|---|---|---|
| 10 | waxy (low-P) | 4 | 59 | |
| 11 | waxy (low-P) | 4 | | 81 |
| 12 | waxy (P-Ø) | 4 | 78 | |
| 13 | waxy (P-Ø) | 4 | | 63 |
| 14 | waxy (low-P) | 25 | 59 | |
| 15 | waxy (low-P) | 25 | | 78 |
| 16 | waxy (P-Ø) | 25 | 79 | |
| 17 | waxy (P-Ø) | 25 | | 61 |

Table 5 shows that by increasing the solids content from 10 to 30% by weight in the paste of debranched low-phosphate waxy potato starch, the RS content in the product can be increased from 59 to approximately 80%, whereas under the same retrogradation conditions, the RS content in the product produced from debranched waxy potato starch having an average bound phosphate content decreases from approximately 79% to approximately 62%.

EXAMPLES 18–26

Effect of Differing Cooling Programs on the RS Content

TABLE 6

Effect of differing retrogradation regime (cooling program) in combination with varying starting materials on the RS content

| Example | Potato starch type (debranched) | Cooling program | Solids content 10% by weight RS [% by weight] | 30% by weight RS [% by weight] |
|---|---|---|---|---|
| 18 | conventional | 1 | 50 | — |
| 19 | waxy (low-P) | 1 | 50 | — |
| 20 | waxy (low-P) | 1 | — | 79 |
| 21 | waxy (low-P) | 2 | — | 68 |
| 22 | waxy (low-P) | 3 | — | 64 |
| 23 | waxy (P-Ø) | 1 | 89 | — |
| 24 | waxy (P-Ø) | 2 | — | 80 |
| 25 | waxy (P-Ø) | 3 | — | 78 |
| 26 | amylose-rich | 1 | 45 | — |

The results in Table 6 illustrate that by changing the cooling rate in combination with solids content, the RS content in the product can be varied.

EXAMPLES 27–42

Characterization of the Thermal Stability of the RS Products

DSC measurements on starches and starch polymers, carried out under conditions of water excess, give endotherms which generally have one peak. The water excess condition is complied with by all DSC measurements carried out. The endothermic peaks of the DSC measurement are characterized in more detail by various parameters ($T_O$, $T_P$, $T_O$ and dH). The onset temperature $T_O$ characterizes the start of the thermal conversion. The temperature which can be read off at the value $T_p$ is that of the maximum thermal conversion of the crystalline material, while $T_O$ is the temperature at which the conversion process is completed (end temperature).

The energy of conversion dH is determined by calculating the peak area. It represents the total energy which is required for the transformation, Results of DSC measurements were used to characterize the thermal stability of the RS products.

The results in Table 7 illustrate the effect of retrogradation conditions (const. temperature, solids content in the paste) on the thermal stability of the end products produced from potato starch of the waxy variety. In Table 8 the results are summarized on the effect on thermal stability of those RS products which were produced by various cooling programs in pastes of debranched amylopectin potato starches,

TABLE 7

Effect of retrogradation conditions on the thermal stability

| Example | Starch type (debranched) | Retrogradation Temperature (° C.) | Solids content (%) | $T_O$ (° C.) | $T_P$ (° C.) | $T_C$ (° C.) | dH (J/g) |
|---|---|---|---|---|---|---|---|
| 27 | waxy (low-P) | 4 | 10 | 81.3 | 104.7 | 112.8 | 5.0 |
|  |  |  |  | 121.5 | 148.8 | 171.5 | 17.4 |
| 28 | waxy (low-P) | 4 | 30 | 82.5 | 107.9 | 118.0 | 4.8 |
|  |  |  |  | 120.6 | 143.3 | — | — |
| 29 | waxy (low-P) | 25 | 10 | 76.8 | 102.7 | 113.5 | 7.9 |
|  |  |  |  | 121.9 | 156.3 | — | — |
| 30 | waxy (low-P) | 25 | 30 | 89.2 | 106.5 | 115.9 | 2.3 |
|  |  |  |  | 122.5 | 142.9 | 166.5 | 4.5 |
| 31 | waxy (P-Ø) | 4 | 10 | 83.0 | 100.3 | 111.4 | 7.6 |
| 32 | waxy (P-Ø) | 4 | 30 | 110.1 | 123.4 | 136.2 | 3.4 |
|  |  |  |  | 142.8 | 156.0 | 176.8 | 2.7 |
| 33 | waxy (P-Ø) | 25 | 10 | 78.8 | 97.5 | 109.8 | 12.2 |
| 34 | waxy (P-Ø) | 25 | 30 | 85.0 | 102.6 | 110.6 | 3.0 |
|  |  |  |  | 110.6 | 124.5 | 133.0 | 1.0 |
|  |  |  |  | 141.7 | 153.6 | 162.4 | 0.7 |

From Table 7 it is clear that virtually all debranched retrograded samples show at (least 2, some even 3, isothermal conversions under the conditions of water excess. The onset temperatures of the second and third isothermal transformations all have a value of $\geq 110$ and $\geq 130°$ C. For the thermal stability of the debranched retrograded waxy potato starch samples, a trend may be derived. Thus it is clear from the results in Table 7 that an increase in the solids content from 10 to 30% in the paste leads to an increase in the thermal stability of the end products.

The effect of the retrogradation temperature on the thermal stability, in contrast, is considerably more complex and can only be assessed in combination with the solids content. Thus, the retrogradation of a 10% strength paste of debranched waxy potato starch at a temperature of 4° C. leads to thermally more stable structures than at a retrogradation temperature of 25° C. However, if the solids content in the paste is additionally increased to 30%, the samples of the low-phosphate debranched waxy potato starch retrograded at room temperature have a higher thermal stability. In contrast, the samples of waxy potato starch (waxy [P-Ø]) retrograded under these conditions are less stable than the samples recrystallized at 4° C.

TABLE 8

Effect of the cooling program and of the solids content on the thermal stability of the RS products.

| Example | Starch type debranched | Retrogradation Cooling program | Solids content (%) | $T_O$ (° C.) | $T_P$ (° C.) | $T_C$ (° C.) | dH (J/g) |
|---|---|---|---|---|---|---|---|
| 35 | waxy (low-P) | 1 | 10 | 87.2 | 107.0 | 118.3 | 4.1 |
|  |  |  |  | 126.4 | 143.6 | 171.8 | 22.3 |
| 36 | waxy (low-P) | 1 | 30 | 82.2 | 126.9 | 170.6 | 38.2 |
| 37 | waxy (low-P) | 2 | 30 | 105.7 | 115.1 | 124.4 | 2.7 |
|  |  |  |  | 130.0 | 145.6 | 168.7 | 4.9 |
| 38 | waxy (low-P) | 3 | 30 | 107.6 | 115.7 | 125.7 | 2.6 |

TABLE 8-continued

Effect of the cooling program and of the solids content on the thermal stability of the RS products.

| Example | Starch type debranched | Retrogradation Cooling program | Solids content (%) | $T_O$ (° C.) | $T_P$ (° C.) | $T_C$ (° C.) | dH (J/g) |
|---|---|---|---|---|---|---|---|
| 39 | waxy (P-Ø) | 1 | 10 | 78.6 | 104.1 | 113.1 | 10.8 |
|  |  |  |  | 133.3 | 146.6 | 172.5 | 14.2 |
| 40 | waxy (P-Ø) annealing | 1 | 10 | 83.1 | 101.8 | 115.2 | 15.1 |
|  |  |  | 30 | 134.2 | 148.2 | 166.6 | 3.0 |
| 41 | waxy (P-Ø) | 2 | 30 | 131.9 | 149.0 | 166.0 | 9.9 |
| 42 | waxy (P-Ø) | 3 | 30 | 106.8 | 117.1 | 131.7 | 6.6 |
|  |  |  |  | 136.2 | 148.0 | 169.5 | 4.9 |

From the examples in Table 8 it is clear that using the cooling programs 2 and 3 highly thermally stable products can be produced which have first DSC onset temperatures ($T_O$) of $\geq 105°$ C. The second DSC onset temperatures all have values $\geq 125°$ C.

What is claimed is:

1. A process for preparing a resistant starch which consists of:
    (a) preparing a suspension of a mixture of a potato starch having an amylose content of about <10% and water; where said potato starch is present in a concentration range of about 5–50%;
    (b) heating and then cooling said suspension to gelatanize said suspension;
    (c) setting the pH of said gelatanized suspension to about 3 to 7.5 and the solids content to about 5–50%;
    (d) treating said potato starch with a debranching enzyme to form an enzymatically debranched starch;
    (e) heating said set suspension to a maximum of 150° C.; and
    (f) gradually cooling said heated suspension at a rate of 0.1 to 10 K/min to obtain the resistant starch.
2. The process for preparing the resistant starch as claimed in claim 1 in which the resultant product is then dried.

3. The process for preparing resistant starch as claimed in claim 1, wherein said starch in step (a) is a genetically modified potato starch.

4. The process for preparing resistant starch as claimed in claim 1, wherein said starch in step(a) is a chemically or physically modified starch produced from a genetically modified potato plant.

5. A resistant starch or resistant starch product of thermal stability having a $T_p$ value of about 95–160° C. obtained by the process of claim 1.

6. The resistant starch or resistant starch product as defined in claim 5 which has a thermal stability of a Tp value of about 145–160° C.

7. A food precursor, food or food composition comprising a resistant starch or a resistant starch product as claimed in claim 5.

8. A fat replacer comprising a resistant starch or a resistant starch product as claimed in claim 5.

9. The process as defined in claim 1 wherein in step (f) said cooling is at a rate of 0.5 to 5 K/mm.

10. The process as defined in claim 1 wherein said cooling step (f) is conducted under the action of a shear force.

11. The process ad defined in claim 1 wherein in step (f) said gradually cooling is to a temperature of about 30 to about 4° C.

\* \* \* \* \*